Oct. 7, 1969 D. L. ARMSTRONG Plant Pat. 2,927
ROSE PLANT
Filed Jan. 17, 1968
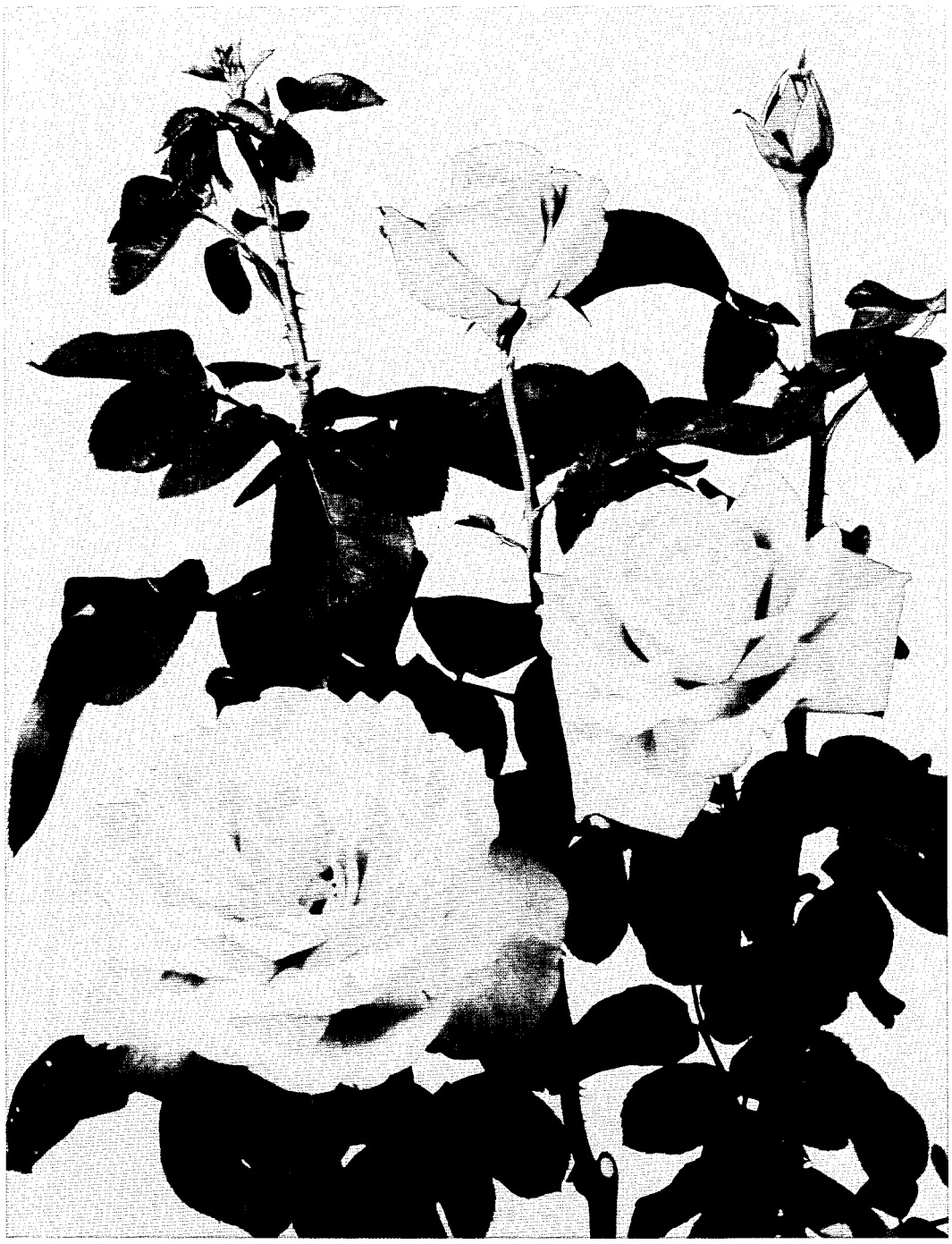
Inventor.
D. L. Armstrong
By: Robb & Robb
Attorneys United States Patent Office Plant Pat. 2,927
Patented Oct. 7, 1969

2,927
ROSE PLANT

David L. Armstrong, Ontario, Calif., assignor to Armstrong Nurseries, Inc., Ontario, Calif., a corporation of California Filed Jan. 17, 1968, Ser. No. 698,671
Int. Cl. A01h 5/02
U.S. Cl. Plt.—20 1 Claim The present invention relates to a new and distinct variety of rose plant of the hybrid tea class, which was originated by me by crossing an unnamed and unpatented rose variety of unidentified parentage with the rose variety known as "Chrysler Imperial" (Plant Patent No. 1,167), the former being the seed parent and the latter being the pollen parent.

The new variety resulted from an extensive breeding program conducted by me and having for its objective the production of new and improved red flowered hybrid tea rose varieties combining the flower qualities of "Chrysler Imperial" with the very vigorous and upright plant habit and strong, long flower stems of the unnamed seed parent. This objective was fully achieved, along with other desirable features, as evidenced by the following unique combination of characteristics which are outstanding in the new variety and which distinguish it from its parents, as well as from all other varieties of which I am aware:

(1) A vigorous and upright plant habit;

(2) Attractive, medium to large, semi-glossy and leathery foliage which covers the plant well and is in good proportion to the size of the stems and flowers;

(3) A habit of bearing the flowers usually singly;

(4) Medium to long flower stems which are borne upright and are particularly notable for their strength and lack of weak necks, considering the size of the flowers, and yet are in excellent proportion to the flowers and foliage;

(5) Large, quite double flowers having an excellent urn-shaped bud form and a graceful, high-centered open flower form resembling that of the parent variety "Chrysler Imperial";

(6) A distinctive and attractive flower color ranging between Cherry and Rose Red; and (7) A strong flower fragrance.

The unnamed seed parent of the new variety is a very vigorous hybrid tea variety, with medium to large, semi-double, red flowers borne on very long, upright, single stems, said flowers being of reasonably good form and having a strong fragrance. The new variety differs from this parent by having a somewhat less vigorous plant habit and shorter flower stems, but the flowers have considerably more petalage, with more perfect urn-shaped buds, more full open flowers and a darker red flower color.

As compared with its pollen parent "Chrysler Imperial," the new variety primarily differs therefrom by having a more vigorous plant habit, a somewhat more upright habit, and longer and stronger flower stems.

A sexual reproduction of my new variety by budding, as performed at Ontario, Calif., shows that the foregoing characteristics and distinctions come true to form and are established and transmitted through succeeding propagations.

The accompanying draing shows typical specimens of the vegatative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Tall; bush; outdoor; seedling; for cut flowers and for garden decoration.

Class: Hybrid tea.

Breeding: Seedling.

*Seed parent.*—An unnamed seedling of unidentified parentage.

*Pollen parents.*—"Chrysler Imperial."

Propagation: Holds its distinguishing characteristics through succeeding propagations by budding.

FLOWER

Locality where grown and observed: Ontario, Calif.

Flowers borne: Usually singly, but sometimes two or three to stem; on strong, medium to long stems.

Quantity of bloom: Free, outdoors.

Continuity: Nearly continuous during growing season.

Fragrance: Strong.

Bud:

*Peduncle.*—From average length to long; heavy; erect; usually smooth; with several to many stipitate glands and none to few small prickles. Color—Near Absinthe Green, Plate XXXI (R).

*Before calyx breaks.*—Size—large. Form—medium length; ovoid.

*As calyx breaks.*—Color—between Dahlia Purple, Plate 931/1, page 178 (W) and Purple Madder, Plate 1028/1, page 181 (W).

*Sepals.*—Sometimes with foliaceous appendages extending ¼ of sepal length. Inner surface—with fine, wooly tomentum. Outer surface—usually smooth. Alternate margins—lined with fine, wooly tomentum. Other margins—with none to few small stipitate glands and small, slender foliaceous parts.

*As first petal opens.*—Size—average. Form—medium length; ovoid; usually urn-shaped. Color: outside—near Chrysanthemum Crimson, Plate 824/3, page 169 (W), blending with near Currant Red, Plate 821/3, page 167 (W) toward base of petal; inside—between Cardinal Red, Plate 822/3, page 168 (W) and Chrysanthemum Crimson, Plate, 824/2, page 169 (W), with small area at base of petal near Aureolin, Plate 3, page 3 (W).

*Opening.*—Opens up well; is not retarded or prevented from opening by cold, hot, wet or dry weather.

Bloom:

*Size (when fully open).*—Large; from 4½ inches to 5½ inches.

*Petalage.*—Double; from 35 to 40 petals, plus 4 to 8 petaloids; arranged irregularly.

*Form.*—High-centered at first, but becoming cupped to high-centered; petals being at first tightly cupped, with tips reflexed lightly outward, but later becoming somewhat loosely cupped at maturity, with tips reflexed outward; intermediate petals of newly opened flower usually rolled outward lightly along apex; outside petals of newly opened flower usually reflexed outward along both apex and edges of petal; outside of petals of three days open flower usually reflexed outward strongly along both apex and edges of petal.

Petals:

*Texture.*—Medium thickness; moderately leathery.

*Appearance.*—Inside—velvety. Outside—satiny.

*Shape.*—Outside—between round and broadly obovate, with apex flat and sometimes with 1 or 2 notches. Intermediate—obovate, with apex rounded and sometimes with 1 or 2 notches. Inside—narrowly obovate, with apex rounded.

This description of a newly opened flower was made from a rose grown outdoors during the month of October at Ontario, Calif.:

*Color.*—Outer petal: outside surface—near Rose Red, Plate 724/2, page 158 (W), with small area at base of petal near Lemon Yellow, Plate 4/1. page 4 (W); inside surface—near Rose Red, Plate 724, page 158 (W), with small area at base of petal near Lemon Yellow, Plate 4, page 4 (W). Intermediate petal: outside surface—near Crimson, Plate 22, page 22 (W); inside surface—near Rose Red, Plate 724, page 158 (W), with small area at base of petal near Aureolin, Plate 3, page 3 (W). Inner petal: outside surface—between Crimson, Plate 22, page 22 (W) and Cherry, Plate 722/1, page 157 (W); inside surface—between Carmine, Plate 21, page 21 (W) and Cherry, Plate 722, page 157 (W), with small area at base of petal near Aureolin, Plate 3, page 3 (W).

This description was made from a rose that was open for three days during the month of October at Ontario, Calif.:

*Color.*—Outer petal: outside surface—near Rose Madder, Plate 23, page 23 (W); inside surface—between Crimson, Plate 22, page 22 (W) and Rose Red, Plate 724/1, page 158 (W), with small area at base of petal near Aureolin, Plate 3/1, page 3 (W). Inner petal: outside surface—between Tyrian Rose, Plate 24/1, page 24 (W) and Tyrian Rose, Plate 24/2, page 24 (W); inside surface—near Rose Red, Plate 724/1, page 158 (W), with small area at base of petal near Aureolin, Plate 3, page 3 (W).

*General color effect.*—Newly opened flower—between Cherry, Plate 722/1, page 157 (W) and Rose Red, Plate 724/1, page 158 (W). Three days open—between Tyrian Rose, Plate 24, page 24 (W) and Rose Red, Plate 724/1, page 158 (W).

*Behavior.*—Drop off cleanly; not particularly affected by cold, hot, wet or dry weather.

*Flower longevity.*—On bush in garden—3 or 4 days in October. Cut roses grown outdoors and kept at living-room temperatures—from 2 to 5 days in October.

REPRODUCTIVE ORGANS

Stamens: From average number to many; arranged regularly about pistils; a few mixed with petaloids.

Filaments: From medium length to long (from 5 mm. to 13 mm. long); most with anthers. Color—near Saturn Red, Plate 13/2, page 13 (W).

Anthers: From medium size to large; all open approximately at once. Color: upper side—margins near Cadmium Orange, Plate 8/1, page 8 (W), with remainder near Lemon Yellow, Plate 4/2, page 4 (W); under side—margins near Cadmium Orange, Plate 8/2, page 8 (W), with remainder near Lemon Yellow, Plate 4/2, page 4 (W).

Pollen: Moderate abundance. Color—near Cadmium Orange, Plate 8/1, page 8 (W).

Pistils: Many (approximately 130 in number).

Styles: Uneven; from short to average length; bunched. Color—upper ⅓ of style near Crimson, Plate 22, page 22 (W), with remainder near Primrose Yellow, Plate 601/3, page 65 (W).

Stigma: Color—near Egyptian Buff, Plate 407, page 122 (W).

Ovaries: Usually all enclosed in calyx.

Hips: Short; globular; smooth; walls thick and fleshy.

Color (½ mature)—near Chrysolite Green, Plate XXXI (R).

Sepals: Falling soon; medium length. Color: inside—near Light Brownish-Drab, Plate XLV (R); outside—near Asphodel Green, Plate XLI (R).

Seeds: Few (from 5 to 10); from small to medium size.

PLANT

Foliage:

*Leaves.*—Compound of 3 to 7 leaflets; abundant; from medium size to large; leathery; semi-glossy.

*Leaflets.*—Shape—oval. Apex—acute. Base—round. Margin—simply serrate.

*Color.*—Mature: upper surface—near Forest Green, Plate XVII (R); under surface—between Biscay Green, Plate XVII (R) and Light Bice Green, Plate XVII (R). Young: upper surface—near Deep Dull Yellow-Green (1), Plate XXXII (R); under surface—near Rainette Green, Plate XXXI (R).

*Rachis (the supporting stem of the compound leaf).*—From average size to heavy. Upper side—grooved; with several stipitate glands on edges. Under side—smooth; with few stipitate glands and few small prickles.

*Stipules.*—Short; medium width; with very short points turning out at an angle of more than 45°.

Growth:

*Habit.*—Upright; moderately branched.

*Growth.*—Vigorous.

*Canes.*—Heavy.

*Main stems.*—Color—near Citrine Drab, Plate XL (R). Large prickles—from several to many; medium length; hooked slightly downward; with medium length, narrow base; Color—near Pecan Brown, Plate XXVIII (R). Small prickles—few; color—near Pecan Brown, Plate XXVIII (R). Hairs—none.

*Branches.*—Color—near Rainette Green, Plate XXXI (R). Large prickles—from several to many; medium length; hooked slightly downward; with medium length, narrow base; color—near Mikado Brown, Plate XXIX (R). Small prickles—few; color—near Mikado Brown, Plate XXIX (R). Hairs—none.

*New shoots.*—Color—near Scheele's Green, Plate VI (R), overlaid with near Ocher Red, Plate XXVII (R) on side exposed to the sun. Large prickles—several; medium length; hooked slightly downward; with short, narrow base; color—near Indian Red, Plate XXVII (R). Small prickles—several; color—near Indian Red, Plate XXVII (R). Hairs—none.

I claim:

1. A new and distinct variety of rose plant of the hybrid tea class, substantially as herein shown and described, characterized particularly as to novelty by the unique combination of a vigorous and upright plant habit, attractive, medium to large semi-glossy and leathery foliage which covers the plant well and is in good proportion to the size of the stems and flowers, a habit of bearing the flowers usually singly, medium to long flower stems which are borne upright and are particularly notable for their strength and lack of weak necks, considering the size of the flowers, and yet are in excellent proportion to the flowers and foliage, large, quite double flowers having an excellent urn-shaped bud form and a graceful, high-centered open flower form resembling that of the parent variety "Chrysler Imperial," a distinctive and attractive flower color ranging between Cherry and Rose Red and a strong flower fragrance.

No references cited.

ROBERT E. BAGWILL, Primary Examiner